United States Patent
Song

(10) Patent No.: US 12,429,768 B2
(45) Date of Patent: Sep. 30, 2025

(54) PHOTOSENSITIZING COMPOUND, PHOTORESIST COMPOSITION INCLUDING THE SAME, AND METHOD OF MANUFACTURING INTEGRATED CIRCUIT DEVICE

(71) Applicant: SAMSUNG ELECTRONICS CO., LTD., Suwon-si (KR)

(72) Inventor: Hyun-Ji Song, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 662 days.

(21) Appl. No.: 17/741,753

(22) Filed: May 11, 2022

(65) Prior Publication Data
US 2023/0060954 A1    Mar. 2, 2023

(30) Foreign Application Priority Data

Aug. 27, 2021  (KR) .................. 10-2021-0113985

(51) Int. Cl.
*G03F 7/004* (2006.01)
*C07C 69/736* (2006.01)

(52) U.S. Cl.
CPC .......... *G03F 7/0045* (2013.01); *C07C 69/736* (2013.01); *C07C 2601/08* (2017.05); *C07C 2601/14* (2017.05); *C07C 2603/74* (2017.05)

(58) Field of Classification Search
CPC ............................ G03F 7/0045; C07C 69/736
See application file for complete search history.

(56) References Cited

U.S. PATENT DOCUMENTS

| 7,355,079 B2 | 4/2008 | Scanlan et al. |
| 7,534,547 B2 | 5/2009 | Hanabata et al. |

(Continued)

FOREIGN PATENT DOCUMENTS

| JP | 6401982 B2 | 10/2018 |
| KR | 10-2021-0094191 A | 7/2021 |

(Continued)

OTHER PUBLICATIONS

Bridoux et al., "Semisynthesis and pharmacological activities of Tetrac analogs: Angiogenesis modulators", 2009, Bioorganic & Medicinal Chemistry Letters, 19, 3259-3263. (Year: 2009).*

(Continued)

*Primary Examiner* — Mark F. Huff
*Assistant Examiner* — Anna Malloy
(74) *Attorney, Agent, or Firm* — Muir Patent Law, PLLC

(57) ABSTRACT

A compound represented by Chemical Formula 1:

$$Ar^1\text{-}L^1\text{-}Ar^2\text{-}L^2\text{-}X\text{—}R^1, \quad \text{[Chemical Formula 1]}$$

in which $Ar^1$ and $Ar^2$ are aromatic rings or heterocyclic aromatic rings that each include at least one iodine atom and $Ar^1$ also includes at least one hydroxyl group, $L^1$ and $L^2$ are each a divalent linking group, X is —C(=O)O— or —S(=O)$_2$—O—, and $R^1$ is an acid-labile protecting group. Photoresist compositions that include the compound, and methods of manufacturing an integrated circuit device by using the photoresist composition.

20 Claims, 6 Drawing Sheets

(56) References Cited

U.S. PATENT DOCUMENTS

| | | | |
|---|---|---|---|
| 8,802,240 B2* | 8/2014 | Davis | A61P 31/04 977/773 |
| 2019/0324368 A1* | 10/2019 | Hatakeyama | G03F 7/2006 |
| 2020/0026188 A1 | 1/2020 | Maruyama | |
| 2020/0050107 A1 | 2/2020 | Hatakeyama et al. | |
| 2020/0241417 A1* | 7/2020 | Hatakeyama | C08F 220/1805 |
| 2021/0223692 A1 | 7/2021 | Song et al. | |
| 2021/0240078 A1 | 8/2021 | Kim et al. | |
| 2021/0240079 A1 | 8/2021 | Park et al. | |
| 2021/0255544 A1 | 8/2021 | Kim et al. | |
| 2021/0263411 A1 | 8/2021 | Kim et al. | |

FOREIGN PATENT DOCUMENTS

| | | |
|---|---|---|
| KR | 10-2021-0096882 A | 8/2021 |
| KR | 10-2021-0099692 A | 8/2021 |
| KR | 10-2021-0100792 A | 8/2021 |
| KR | 10-2021-0100797 A | 8/2021 |
| WO | WO 2008/120743 A1 | 10/2008 |

OTHER PUBLICATIONS

Rajabi et al., "Synthesis of new analogs of tetraiodothyroacetic acid (tetrac) as novel angiogenesis inhibitors for treatment of cancer," Bioorganic & Medicinal Chemistry Letters, 28, 1223-1227 (2018).
Bridoux et al., "Semisynthesis and pharmacological activities of Tetrac analogs: Angiogenesis modulators," Bioorganic & Medicinal Chemistry Letters, 19, 3259-3263 (2009).
T296125 Product Details, Toronto Research Chemicals, Apr. 23, 2021.

* cited by examiner

PHOTOSENSITIZING COMPOUND, PHOTORESIST COMPOSITION INCLUDING THE SAME, AND METHOD OF MANUFACTURING INTEGRATED CIRCUIT DEVICE

CROSS-REFERENCE TO RELATED APPLICATION

This application is based on and claims priority under 35 U.S.C. § 119 to Korean Patent Application No. 10-2021-0113985, filed on Aug. 27, 2021, in the Korean Intellectual Property (Office, the disclosure of which is incorporated by reference herein in its entirety.

BACKGROUND

1. Field

Embodiments relate to a photosensitizing compound, a photoresist composition including the photosensitizing compound, and a method of manufacturing an integrated circuit device.

2. Description of the Related Art

Due to the development of electronics technology, semiconductor devices have been rapidly down-scaled in recent years. Thus, photolithography processes having advantages in implementing fine patterns have been required.

SUMMARY

The embodiments may be realized by providing a compound represented by Chemical Formula 1:

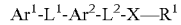   [Chemical Formula 1]

wherein, in Chemical Formula 1, $Ar^1$ is an organic group including a C6 to C30 aromatic ring, which includes at least one iodine atom and at least one hydroxyl group, or a C6 to C30 heterocyclic aromatic ring, which includes at least one iodine atom and at least one hydroxyl group, $Ar^2$ is an organic group including a C6 to C30 aromatic ring, which includes at least one iodine atom, or a C6 to C30 heterocyclic aromatic ring, which includes at least one iodine atom, $L^1$ and L are each independently a divalent linking group, the divalent linking group including —O—, —S—, —SO—, —SO$_2$—, —CO—, —O—CO—O—, —C(=O)O—, —OCO—, —CONH—, —NHCO—, —CO—, a substituted or unsubstituted C1 to C6 linear alkylene group, a substituted or unsubstituted C3 to C6 branched alkylene group, a substituted or unsubstituted C3 to C15 cycloalkylene group, a substituted or unsubstituted C2 to C6 alkenylene group, or a combination thereof, X is —C(=O)O— or —S(=O)$_2$—O—, and $R^1$ is an acid-labile protecting group including a substituted or unsubstituted t-butyl group or a substituted or unsubstituted C$_3$ to C30 tertiary alicyclic group.

The embodiments may be realized by providing a photoresist composition including a compound; a chemically amplified polymer; a photoacid generator (PAG); and a solvent, wherein the compound is represented by Chemical Formula 1:

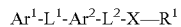   [Chemical Formula 1]

wherein, in Chemical Formula 1, $Ar^1$ is an organic group including a C6 to C30 aromatic ring, which includes at least one iodine atom and at least one hydroxyl group, or a C6 to C30 heterocyclic aromatic ring, which includes at least one iodine atom and at least one hydroxyl group. $Ar^2$ is an organic group including a C6 to C30 aromatic ring, which includes at least one iodine atom, or a C6 to C30 heterocyclic aromatic ring, which includes at least one iodine atom, $L^1$ and $L^2$ are each independently a divalent linking group, the divalent linking group including —O—, —S—, —SO—, —SO$_2$—, —CO—, —O—CO—O—, —C(=O)O—, —OCO—, —CONH—, —NHCO—, —CO—, a substituted or unsubstituted C1 to C6 linear alkylene group, a substituted or unsubstituted C3 to C6 branched alkylene group, a substituted or unsubstituted C3 to C15 cycloalkylene group, a substituted or unsubstituted C2 to C6 alkenylene group, or a combination thereof, X is —C(=O)O— or —S(=O)$_2$—O—, and $R^1$ is an acid-labile protecting group including a substituted or unsubstituted t-butyl group or a substituted or unsubstituted C3 to C30 tertiary alicyclic group.

The embodiments may be realized by providing a method of manufacturing an integrated circuit device, the method including forming a photoresist layer on an underlayer by using a photoresist composition including a compound, a chemically amplified polymer, a photoacid generator (PAG), and a solvent, the compound including a phenolic hydroxyl group, a plurality of iodine atoms, and an acid-labile protecting group; generating a plurality of acids from the phenolic hydroxyl group and the PAG in a first region of the photoresist layer by exposing the first region, and deprotecting the chemically amplified polymer and the compound by the plurality of acids; forming a photoresist pattern including an unexposed region of the photoresist layer by removing the exposed first region of the photoresist layer by using a developer; and processing the underlayer by using the photoresist pattern.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
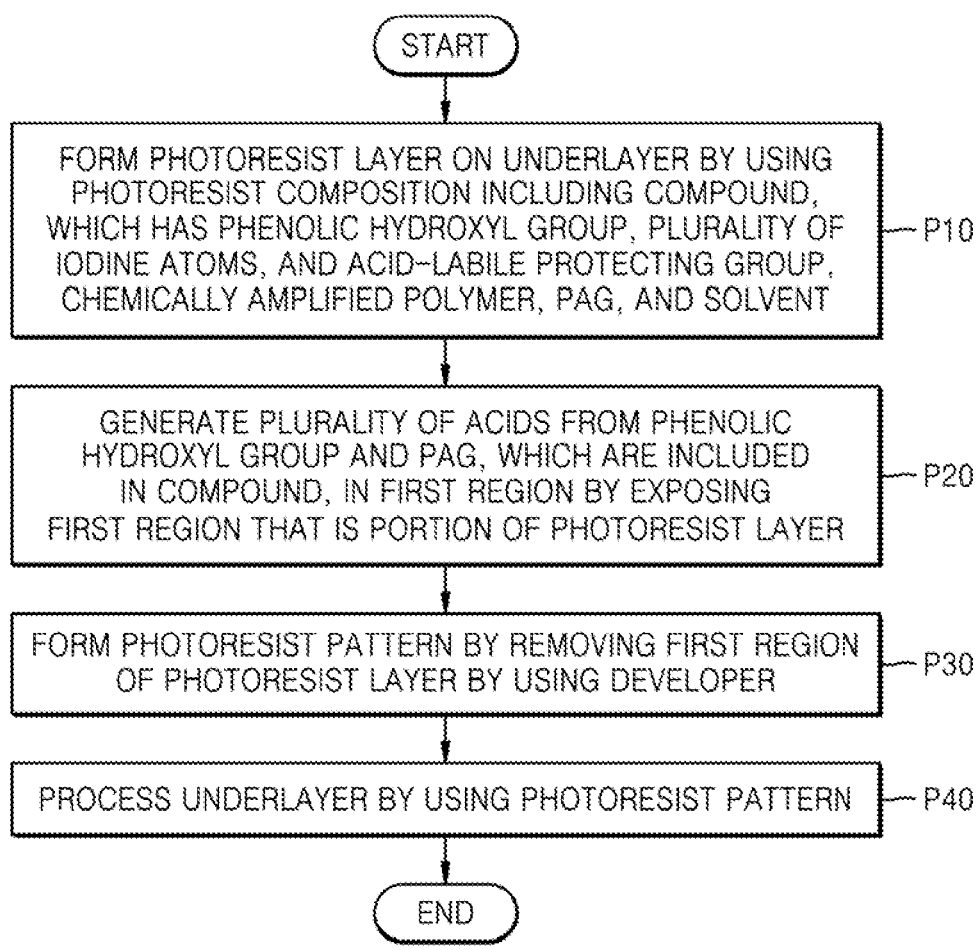
FIG. 1 is a flowchart of a method of manufacturing an integrated circuit device, according to embodiments.

A compound according to embodiments includes a phenolic hydroxyl group, a plurality of iodine atoms, and an acid-labile protecting group. In an implementation, the compound is represented by Chemical Formula 1.

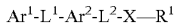   [Chemical Formula 1]

In Chemical Formula 1, according to an embodiment, $Ar^1$ is an organic group including a C6 to C30 aromatic ring or a C6 to C30 heterocyclic aromatic ring. In an implementation, the C6 to C30 aromatic ring or the C6 to C30 heterocyclic aromatic ring includes at least one iodine atom and at least one hydroxyl group.

According to an embodiment, $Ar^2$ is an organic group including a C6 to C30 aromatic ring or a C6 to C30 heterocyclic aromatic ring. In an implementation, the C6 to C30 aromatic ring or C6 to C30 heterocyclic aromatic ring includes at least one iodine atom.

According to an embodiment, $L^1$ and $L^2$ are each independently a 2-valent or divalent linking group. In an implementation, the divalent linking group includes —O—, —S—, —SO—, —SO$_2$—, —CO—, —O—CO—O—, —C(=O)O—, —OCO—, —CONH—, —NHCO—, —CO—, a substituted or unsubstituted C1 to C6 linear alkylene group, a substituted or unsubstituted C3 to C6 branched alkylene group, a substituted or unsubstituted C3 to C15 cycloalkylene group, a substituted or unsubstituted C2 to C6 alkenylene group, or a combination thereof.

In an embodiment, X is —C(=O)O— or —S(=O)$_2$—O—.

In an embodiment, $R^1$ is an acid-labile protecting group. In an implementation, the acid-labile protecting group includes a substituted or unsubstituted t-butyl group or a substituted or unsubstituted C3 to C30 tertiary alicyclic group.

As used herein, the term "substituted" refers to including at least one substituent, e.g., a halogen atom (a F atom, a Cl atom, a Br atom, or an I atom), a hydroxyl group, an amino group, a thiol group, a carboxyl group, a carboxylate group, an ester group, an amide group, a nitrile group, a sulfide group, a disulfide group, a nitro group, a C1 to C20 alkyl group, a C1 to C20 cycloalkyl group, a C2 to C20 alkenyl group, a C1 to C20 alkoxy group, a C2 to C20 alkenoxy group, a C6 to C30 aryl group, a C6 to C30 aryloxy group, a C7 to C30 alkylaryl group, or a C7 to C30 alkylaryloxy group, unless otherwise defined. As used herein, the term "or" is not an exclusive term, e.g., "A or B" would include A, B, or A and B.

As used herein, the compound represented by Chemical Formula 1 may be referred to as a photosensitizing compound.

In an implementation, in Chemical Formula 1, $Ar^1$ and $Ar^2$ may each independently include. e.g., a phenyl group, a naphthyl group, an anthracenyl group, a phenanthrenyl group, a pyrenyl group, a perylenyl group, a chrysenyl group, or a triphenylenyl group, as the C6 to C30 aromatic group.

In an implementation, in Chemical Formula 1, $Ar^1$ may have, e.g., a structure of Chemical Formula 1A or Chemical Formula 1B.

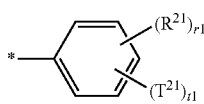

[Chemical Formula 1A]

In Chemical Formula 1A, $R^{21}$ may be, e.g., an iodine atom, $T^{21}$ may be, e.g., a hydroxyl group, r1 may be, e.g., an integer of 2 to 4, t1 may be, e.g., an integer of 1 to 3, and "*" represents a binding site.

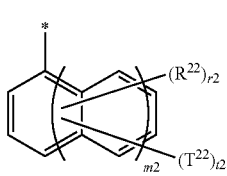

[Chemical Formula 1B]

In Chemical Formula 1B, $R^{22}$ may be, e.g., an iodine atom; $T^{22}$ may be, e.g., a hydroxyl group; m2 may be, e.g., 1 or 2; when m2=1, r2 may be, e.g., an integer of 2 to 6 and t2 may be, e.g., an integer of 1 to 5, and "*" represents a binding site. In an implementation, when m2=2, r2 may be, e.g., an integer of 2 to 8 and t2 may be, e.g., an integer of 1 to 7.

In an implementation, in Chemical Formula 1, $Ar^2$ may have. e.g., a structure of Chemical Formula 1C.

[Chemical Formula 1C]

In Chemical Formula 1C, $R^{23}$ may be, e.g., an iodine atom, $T^{23}$ may be, e.g., a hydroxyl group, r3 may be, e.g., 2 or 3, t3 may be, e.g., 1 or 2, and "*" represents a binding site.

In an implementation, in Chemical Formula 1, at least one of $Ar^1$ and $Ar^2$ may include, e.g., a C6 to C30 heterocyclic aromatic group. The C6 to C30 heterocyclic aromatic group may include, e.g., a monocyclic aromatic ring substituted with at least one of a nitrogen atom, an oxygen atom, and a sulfur atom, or include a polycyclic aromatic ring substituted with at least one of a nitrogen atom, an oxygen atom, and a sulfur atom. In an implementation, the heterocyclic aromatic group may have a structure derived from fused rings including pyridine, pyrazine, pyrimidine, pyridazine, and combinations thereof.

In an implementation, in Chemical Formula 1, a total number of iodine atoms included in $Ar^1$ and $Ar^2$ may be, e.g., at least 4.

In an implementation, in Chemical Formula 1, each of $L^1$ and $L^2$ may be a 2-valent linking group substituted with a halogen atom. In this case, the halogen atom may be a fluorine atom or a chlorine atom.

In an implementation, in Chemical Formula 1, $L^1$ may be, e.g., —O—, —S—, —CH$_2$—, —CF$_2$—, —CHF—, —CCl$_2$—, —CH—CHCl—, —CH$_2$CF$_2$—, or (CH$_2$)$_m$(CF$_2$)$_n$— (in which each of m and n is an integer of 1 to 5, and 2≤(m+n)≤6). In an implementation, in Chemical Formula 1, $L^2$ may be, e.g., —CH$_2$—, —CF$_2$—, —CHF—, —CCl—, —CH—CHCl—, —CH$_2$CF$_2$—, or (CH$_2$)$_m$CF$_2$)$_n$— (in which each of m and n is an integer of 1 to 5, and 2≤(m+n)≤6). In an implementation, in Chemical Formula 1, $L^1$ may be, e.g., —O—, and $L^2$ may be, e.g., —C(=O)O—.

In an implementation, in Chemical Formula 1, $R^1$ may be, e.g., an acid-labile protecting group having an unsubstituted structure. In an implementation, $R^1$ may include, e.g., an unsubstituted t-butyl group or an unsubstituted C3 to C30 tertiary alicyclic group.

In an implementation, in Chemical Formula 1, $R^1$ may be, e.g., an acid-labile protecting group having a structure substituted with a first substituent. In an implementation, $R^1$ may include, e.g., a t-butyl group substituted with a first substituent, or a C3 to C30 tertiary alicyclic group substituted with a first substituent. The first substituent may include, e.g., a C1 to C10 alkyl group, a C1 to C10 alkoxy group, a halogen atom, a C1 to C10 alkyl halide group, a hydroxyl group, an unsubstituted C6 to C30 aryl group, or a C6 to C30 aryl group in which some of carbon atoms constituting the first substituent are substituted with a halogen atom-containing or heteroatom-containing group. The halogen atom, which may be included in the first substituent, may include, e.g., a F atom, a Cl atom, a Br atom, or an I atom. The alkyl halide group may include at least one halogen atom. e.g., a F atom, a Cl atom, a Br atom, or an I atom. The heteroatom may be, e.g., an oxygen atom, a sulfur atom, or a nitrogen atom. In an implementation, the heteroatom-containing group may be, e.g., —O—, —C(=O)—O—, —O—C(=O), —C(=O)—, —O—C(=O)—O—, —C(=O)—NH—, —NH—, —S—, —S(=O)$_2$—, or —S(=O)$_2$—O—.

In an implementation, in Chemical Formula 1, $R^1$ may be, e.g., a tertiary alicyclic group including a cyclic aliphatic hydrocarbon group, and the cyclic aliphatic hydrocarbon group may include a group in which two hydrogen atoms are excluded from a C3 to C6 monocycloalkane. In an implementation, $R^1$ may be, e.g., a tertiary alicyclic group including a cyclic aliphatic hydrocarbon group, and the cyclic aliphatic hydrocarbon group may include a group in which two hydrogen atoms are excluded from a C7 to C12 polycycloalkane.

In an implementation, in Chemical Formula 1, $R^1$ may have, e.g., one of the following structures.

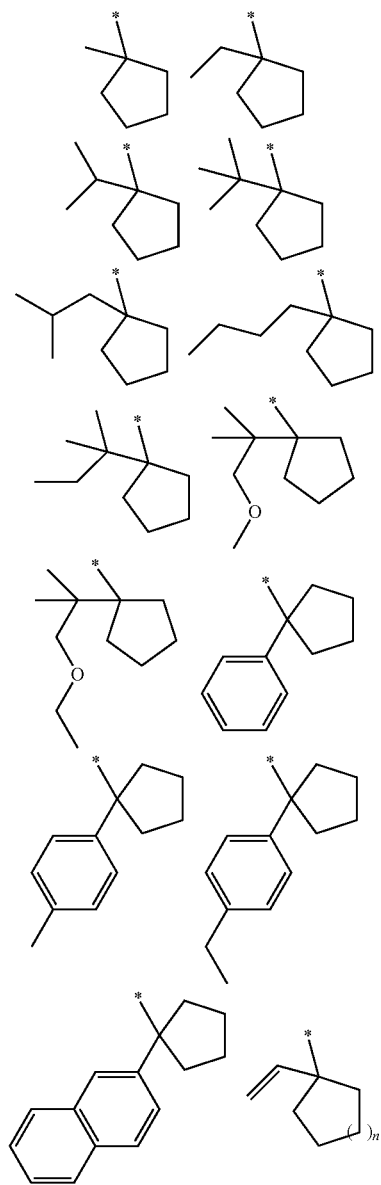

-continued
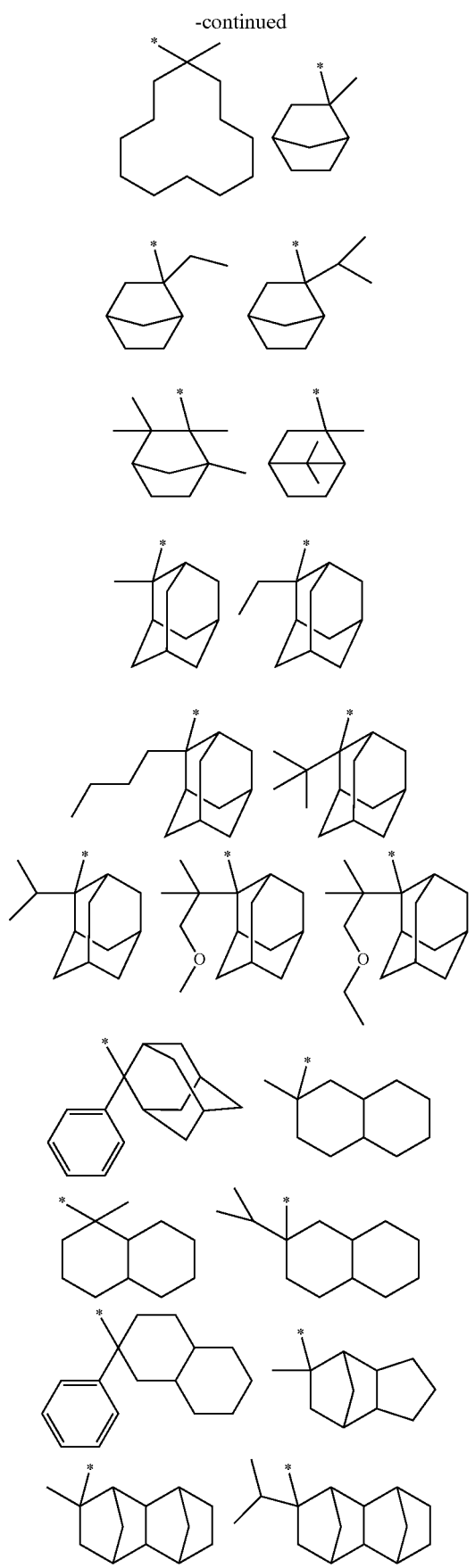
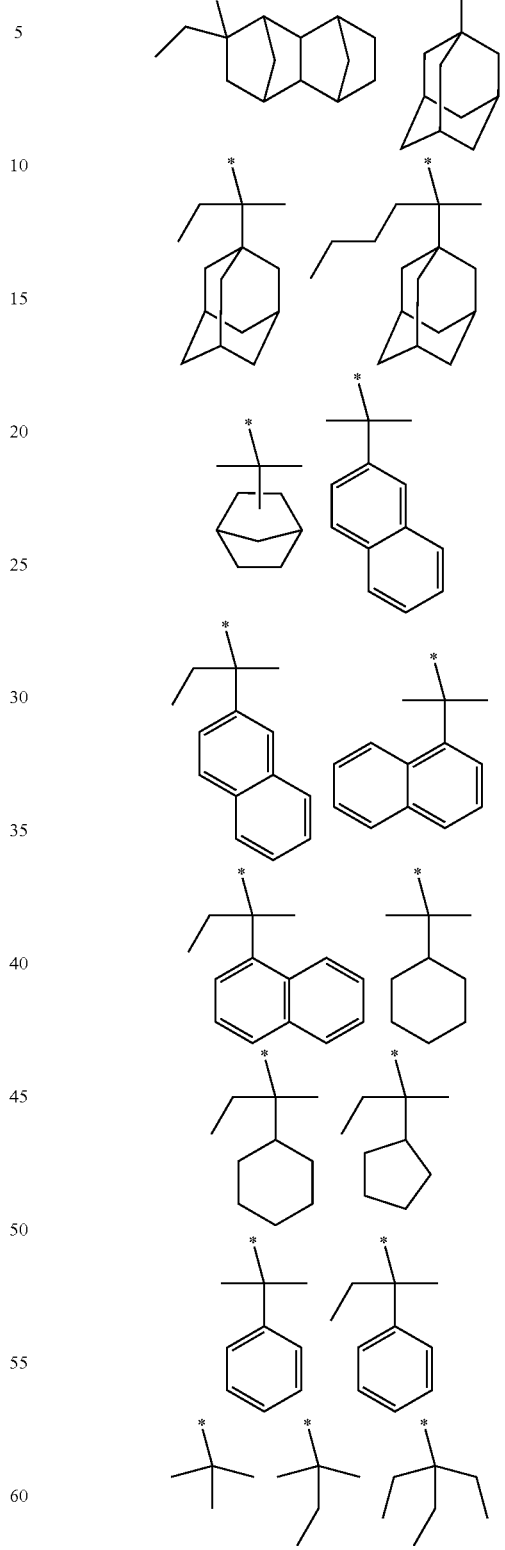
In the above structures, n may be, e.g., an integer of 1 to 11, and "*" represents a binding site.
In an implementation, the compound may be, e.g., represented by Chemical Formula 2.

[Chemical Formula 2]

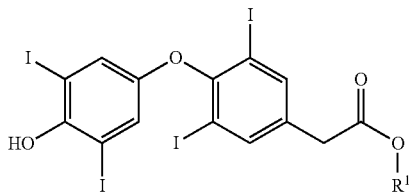

In Chemical Formula 2, $R^1$ may be defined the same as that of Chemical Formula 1.

In an implementation, a total amount (e.g., weight) of iodine atoms included in the compound having the structure of Chemical Formula 2 may be at least 50% by weight (wt %), based on a total weight of the compound. In an implementation, in Chemical Formula 2, when $R^1$ is a t-butyl group, the total amount of the iodine atoms included in the compound may be, e.g., about 63.1 wt %. In an implementation, in Chemical Formula 2, when $R^1$ is an isopropylcyclopentyl group, the total amount of the iodine atoms included in the compound may be, e.g., about 59.2 wt %. In an implementation, in Chemical Formula 2, when $R^1$ is an isopropyladamantyl group, the total amount of the iodine atoms included in the compound may be, e.g., about 54.9 wt %.

In an implementation, the compound may be represented by, e.g., one of the following Chemical Formulae 2A to 2E.

[Chemical Formula 2A]

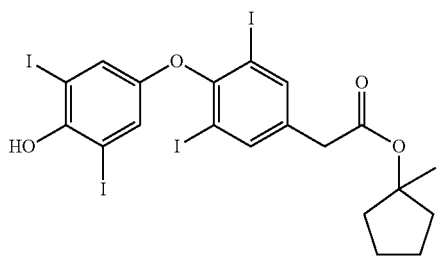

[Chemical Formula 2B]

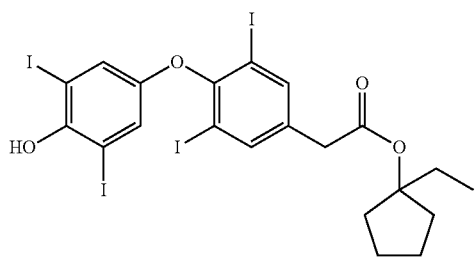

[Chemical Formula 2C]

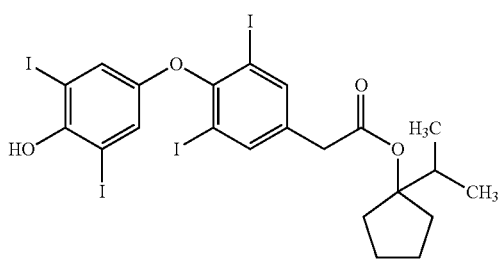

[Chemical Formula 2D]

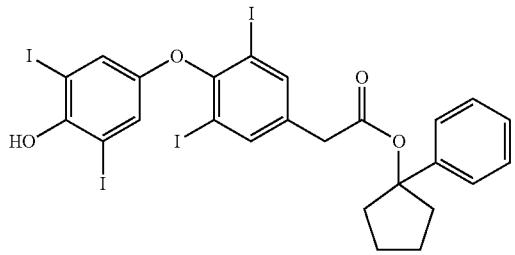

[Chemical Formula 2E]

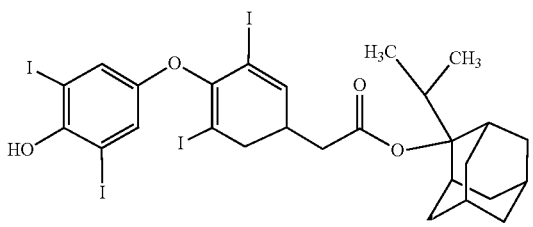

A photoresist composition according to an embodiment may include, e.g., a compound (which includes a phenolic hydroxyl group, a plurality of iodine atoms, and an acid-labile protecting group), a chemically amplified polymer, a photoacid generator (PAG), and a solvent. The compound may be, e.g., a photosensitizing compound having the structure represented by Chemical Formula 1. A reference for detailed configurations of the photosensitizing compound, which has the structure represented by Chemical Formula 1, may be made to the above descriptions thereof.

In the photoresist composition according to embodiments, the photosensitizing compound represented by Chemical Formula 1 may be present in an amount of, e.g., about 1 wt % to about 100 wt %, about 1 wt % to about 50 wt %, or about 5 wt % to about 30 wt %, based on a total weight of the chemically amplified polymer.

In the photoresist composition according to embodiments, the chemically amplified polymer may include a polymer including a repeating unit that may change in solubility thereof in a developer due to an action of an acid. The chemically amplified polymer may be a block copolymer or a random copolymer. In an implementation, the chemically amplified polymer may include a positive photoresist. The positive photoresist may include, e.g., a photoresist for KrF excimer lasers (248 nm), a photoresist for ArF excimer lasers (193 nm), a photoresist for $F_2$ excimer lasers (157 nm), or a photoresist for extreme ultraviolet (EUV) (13.5 nm).

In an implementation, the chemically amplified polymer may include a repeating unit that is decomposed by an action of an acid and thus increases the solubility thereof in a developer. In an implementation, the chemically amplified polymer may include a repeating unit that is decomposed by an action of an acid and thus generates a phenolic acid or generates a Brønsted acid corresponding thereto. In an implementation, the chemically amplified polymer may include a first repeating unit derived from hydroxystyrene or a hydroxystyrene derivative. The hydroxystyrene derivative may include hydroxystyrenes in which a hydrogen atom at an α-site is substituted with a C1 to C5 alkyl group or a C1 to C5 alkyl halide group, or derivatives thereof. In an implementation, the first repeating unit may be derived from 3-hydroxystyrene, 4-hydroxystyrene, 5-hydroxy-2-vinylnaphthalene, or 6-hydroxy-2-vinylnaphthalene.

In an implementation, the chemically amplified polymer may have a structure in which the first repeating unit derived from hydroxystyrene or a hydroxystyrene derivative is copolymerized with at least one second repeating unit having an acid-labile protecting group. The at least one second repeating unit may include a (meth)acrylate polymer. In an implementation, the at least one second repeating unit may include polymethylmethacrylate (PMMA) poly(t-butylmethacrylate), poly(methacrylic acid), poly(norbomylmethacrylate), or a binary or ternary copolymer of repeating units of the (meth)acrylate polymers set forth above.

In an implementation, the chemically amplified polymer may include a blend of a first polymer, which has the first repeating unit, and a second polymer, which has the at least one second repeating unit.

The acid-labile group, which may be included in the at least one second repeating unit, may include, e.g., a tert-butoxycarbonyl (t-BOC) group, an isonorbonyl group, a 2-methyl-2-adamantyl group, a 2-ethyl-2-adamantyl group, a 3-tetrahydrofuranyl group, a 3-oxocyclohexyl group, a 1-butylolactone-3-yl group, a mavaloniclactone group, a γ-butyrolactone-2-yl group, a 3-methyl-γ-butyrolactone-3-yl group, a 2-tetrahydropyranyl group, a 2-tetrahydrofuranyl group, a 2,3-propylenecarbonate-1-yl group, a 1-methoxyethyl group, a 1-ethoxyethyl group, a 1-(2-methoxyethoxy) ethyl group, a 1-(2-acetoxyethoxy)ethyl group, a t-buthoxycarbonylmethyl group, a methoxymethyl group, an ethoxymethyl group, a trimethoxysilyl group, or a triethoxysilyl group.

In an implementation, the chemically amplified polymer may further include at least one of a third repeating unit, which has an acrylate derivative substituent including a hydroxyl group, and a fourth repeating unit, which has a protecting group substituted with fluorine.

The chemically amplified polymer may have a weight-average molecular weight of, e.g., about 1,000 to about 500,000. In the photoresist composition, the chemically amplified polymer may be present in an amount of, e.g., about 1 wt % to about 25 wt %, based on the total weight of the photoresist composition. Maintaining the amount of the chemically amplified polymer at about 1 wt % or greater may facilitate coating of the photoresist composition. Maintaining the amount of the chemically amplified polymer is at about 25 wt % or less may help ensure that the viscosity of the photoresist composition is not too high, thereby facilitating uniform coating of the photoresist composition.

In the photoresist composition according to embodiments, the PAG may generate an acid when exposed to, e.g., a KrF excimer laser (248 nm), an ArF excimer laser (193 nm), an $F_2$ excimer laser (157 nm), or an EUV laser (13.5 nm). The PAG may include a material generating a relatively strong acid having an acid dissociation constant (pKa) that is equal to or greater than about −20 and is less than about 1. The PAG may include, e.g., triarylsulfonium salts, daryliodonium salts, sulfonates, or mixtures thereof. In an implementation, the PAG may include, e.g., triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyl-diphenyliodonium nonaflate, N-hydroxysuccinimide nonaflate, norbornene-dicarboximide-nonaflate, triphenylsulfonium perfluorobutanesulfonate, triphenylsulfonium perfluorooctanesulfonate (PFOS), diphenyliodonium PFOS, methoxydiphenyliodonium PFOS, di-t-butyldiphenyliodonium triflate, N-hydroxysuccinimide PFOS, norbornene-dicarboximide PFOS, or a mixture thereof.

In the photoresist composition according to embodiments, the PAG may be present in an amount of, e.g., about 0.1 wt % to about 5.0 wt %, based on the total weight of the chemically amplified polymer.

In an implementation, the photoresist composition may further include, e.g., a basic quencher.

The basic quencher may include a compound capable of trapping acids generated from the photosensitizing compound or the PAG, which is included in the photoresist composition according to embodiments, when the acids diffuse in unexposed regions of a photoresist layer. The basic quencher may be included in the photoresist composition, thereby suppressing a diffusion rate of the acids.

In an implementation, the basic quencher may include, e.g., a primary aliphatic amine, a secondary aliphatic amine, a tertiary aliphatic amine, an aromatic amine, a heterocyclic ring-containing amine, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amides, imides, carbamates, or ammonium salts. In an implementation, the basic quencher may include, e.g., triethanol amine, triethyl amine, tributyl amine, tripropyl amine, hexamethyl disilazan, aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine, or a combination thereof.

In an implementation, the basic quencher may include a photodegradable base. The photodegradable base may include a compound that generates acids by exposure and neutralizes acids before exposure. The photodegradable base may lose the function of trapping acids when decomposed by exposure. Accordingly, when some regions of a photoresist layer formed from the chemically amplified photoresist composition, which includes the basic quencher including the photodegradable base, are exposed to light, the photodegradable base in the exposed regions of the photoresist layer may lose alkalinity, and the photodegradable base in unexposed regions of the photoresist layer may trap acids and thus suppress the diffusion of the acids into the unexposed regions from the exposed regions.

The photodegradable base may include a carboxylate or sulfonate salt of a photodegradable cation. In an implementation, the photodegradable cation may form a complex with an anion of a C1 to C20 carboxylic acid. The carboxylic acid may include, e.g., formic acid, acetic acid, propionic acid, tartaric acid, succinic acid, cyclohexylcarboxylic acid, benzoic acid, or salicylic acid.

In the photoresist composition according to embodiments, the basic quencher may be present in an amount of, e.g., about 0.01 wt % to about 5.0 wt %, based on the total weight of the chemically amplified polymer.

In the photoresist composition according to embodiments, the solvent may include an organic solvent. In an implementation, the solvent may include. e.g., ethers, alcohols, aromatic hydrocarbon compounds, ketones, or esters. In an implementation, the solvent may include, e.g., ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol monomethyl ether, propylene glycol monomethyl ether acetate, propylene glycol monoethyl ether, propylene glycol monoethyl ether acetate, propylene glycol propyl ether acetate, propylene glycol monobutyl ether, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactoate, butyl lactoate, or the like. These solvents may be used alone or in combination. In an implementation, an amount of the solvent in the photoresist composition may be adjusted such that solids are present in an amount of about 3 wt % to about 20 wt % in the photoresist composition.

In an implementation, the photoresist composition may further include, e.g., a surfactant.

The surfactant may include, e.g., fluoroalkylbenzene sulfonates, fluoroalkyl carboxylates, fluoroalkyl polyoxyethylene ethers, fluoroalkyl ammonium iodides, fluoroalkyl betaines, fluoroalkyl sulfonates, diglycerin tetrakis(fluoroalkyl polyoxyethylene ethers), fluoroalkyl trimethylammonium salts, fluoroalkyl aminosulfonates, polyoxyethylene nonylphenyl ether, polyoxyethylene octylphenyl ether, polyoxyethylene alkyl ethers, polyoxyethylene lauryl ether, polyoxyethylene oleyl ether, polyoxyethylene tridecyl ether, polyoxyethylene cetyl ether, polyoxyethylene stearyl ether, polyoxyethylene laurate, polyoxyethylene oleate, polyoxyethylene stearate, polyoxyethylene laurylamine, sorbitan laurate, sorbitan palmitate, sorbitan stearate, sorbitan oleate, sorbitan fatty acid esters, polyoxyethylene sorbitan laurate, polyoxyethylene sorbitan palmitate, polyoxyethylene sorbitan stearate, polyoxyethylene sorbitan oleate, polyoxyethylene naphthyl ether, alkylbenzene sulfonates, or alkyl diphenyl ether disulfonates. The surfactant may be present in an amount of, e.g., about 0.001 wt % to about 0.1 wt %, based on the total weight of the chemically amplified polymer.

In an implementation, the photoresist composition may further include, e.g., a pigment, a preservative, an adhesion promoter, a coating aid, a plasticizer, a surface modifying agent, or a dissolution inhibitor.

In an implementation, the photoresist composition according to embodiments may include a compound, which includes a phenolic hydroxyl group, a plurality of iodine atoms, and an acid-labile protecting group and has a structure represented by Chemical Formula 1. In the photoresist composition according to embodiments, the compound represented by Chemical Formula 1 may function as a photosensitizing compound that has excellent sensitivity with respect to an exposure light source and excellent optical absorption properties.

In an implementation, an EUV lithography technique using an exposure process by EUV having a wavelength of about 13.5 nm is a next-generation technique substituting lithography processes using KrF excimer lasers (248 nm) and ArF excimer lasers (193 nm), and various studies about the EUV lithography technique have been carried out. An EUV lithography process has a different operation mechanism from the lithography processes using KrF excimer lasers and ArF excimer lasers. All processes in the EUV lithography process are performed in a vacuum. In EUV lithography equipment, because a light source is lacking in power required for laser irradiation, there is a limit in increasing a dose to a high level enough for a sufficient amount of acids to be generated from a PAG among components of a photoresist composition upon exposure. Thus, when the EUV lithography process is performed by using some other photoresist compositions including a PAG, the efficiency of acid generation from the PAG may be low due to a relatively low dose provided by a light source of the EUV lithography equipment. Accordingly, it may be difficult to obtain desired exposure sensitivity.

In a photolithography process using a photoresist composition including the compound according to an embodiment, when some regions of a photoresist layer obtained from the photoresist composition are exposed to light, the absorbance may be increased due to the compound that has the structure of Chemical Formula 1, e.g., the photosensitizing compound according to embodiments, and thus, the light quantum yield allowing acids to be generated in the exposed regions may be increased. In addition, the acid-labile protecting group included in the compound may be deprotected by the acids generated by the exposure, and thus, may be decomposed into a molecule having a carboxyl group (*—COOH), thereby improving the solubility thereof in a developer. Further, the compound according to embodiments may include the phenolic hydroxyl group, and thus, may have increased sensitivity with respect to an exposure light source. Accordingly, when a photolithography process for manufacturing an integrated circuit device is performed by using the photoresist composition according to embodiments, the photosensitivity may be increased, and the dissolution contrast between the exposed regions and the unexposed regions of the photoresist layer with respect to the developer may be sufficiently secured, thereby improving the resolution in the photolithography process. Therefore, by manufacturing an integrated circuit device by using the photoresist composition according to the embodiments, the dimension precision of a pattern required for the integrated circuit device may be improved, and the productivity of a process of manufacturing the integrated circuit device may be improved.

Hereinafter, an example method of manufacturing an integrated circuit device, according to an embodiment, will be described with reference to the accompanying drawings.

FIG. 1 is a flowchart of a method of manufacturing an integrated circuit device, according to embodiments. FIGS. 2A to 2E are cross-sectional views of stages in a method of manufacturing an integrated circuit device, according to embodiments.

Figure 2A:
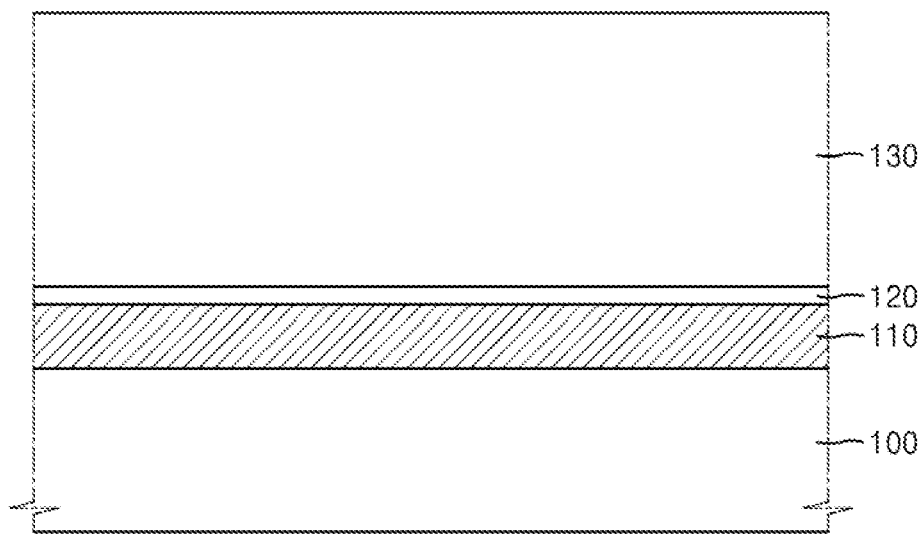
FIGS. 2A to 2E are cross-sectional views of stages in a method of manufacturing an integrated circuit device, according to embodiments.

Referring to FIGS. 1 and 2A, in a process P10 of FIG. 1, a photoresist layer 130 may be formed on an underlayer. The underlayer may include a substrate 100 and a feature layer 110 formed on the substrate 100.

The substrate 100 may include a semiconductor substrate. In an implementation, the substrate 100 may include a semiconductor material such as Si or Ge, or a compound semiconductor material such as SiGe, SiC, GaAs, InAs, or InP.

The feature layer 110 may be an insulating layer, a conductive layer, or a semiconductor layer. In an implementation, the feature layer 110 may include. e.g., a metal, an alloy, a metal carbide, a metal nitride, a metal oxynitride, a metal oxycarbide, a semiconductor, polysilicon, oxide, nitride, oxynitride, or a combination thereof.

In an implementation, as shown in FIG. 2A, before the photoresist layer 130 is formed on the feature layer 110, a developable bottom anti-reflective coating (DBARC) layer 120 may be formed on the feature layer 110. In this case, the photoresist layer 130 may be formed on the DBARC layer 120. The DBARC layer 120 may control the diffuse reflection of light from a light source used upon an exposure process for manufacturing an integrated circuit device, or may absorb light reflected by the feature layer 110 thereunder. In an implementation, the DBARC layer 120 may include an organic anti-reflective coating (ARC) material for KrF excimer lasers, ArF excimer lasers, or other light sources. In an implementation, the DBARC layer 120 may include an organic component having an optical absorption structure. The optical absorption structure may include. e.g., a hydrocarbon compound having one or more benzene rings or having a structure in which benzene rings are fused. The DBARC layer 120 may have, e.g., a thickness of about 20 nm to about 100 nm. In an implementation, the DBARC layer 120 may be omitted.

To form the photoresist layer 130, a photoresist composition including a compound according to Chemical Formula 1, a chemically amplified polymer, a PAG, and a solvent may be used. In an implementation, the compound according to Chemical Formula 1 may include a phenolic hydroxyl group, a plurality of iodine atoms, and an acid-labile protecting group. In an implementation, the photoresist composition may further include a basic quencher. More detailed descriptions of the compound according to Chemical Formula 1 and the photoresist composition are as given above.

To form the photoresist layer 130, the photoresist composition according to the embodiments may be coated on the DBARC layer 120 and then be heat-treated. The coating may be performed by a method such as spin coating, spray coating, dip coating, or the like. The process of heat-treating the photoresist composition may be performed, e.g., at a temperature of about 80° C. to about 300° C. for about 10 seconds to about 100 seconds. The thickness of the photoresist layer 130 may be tens to hundreds of times the thickness of the DBARC layer 120. The photoresist layer 130 may have, e.g., a thickness of about 100 nm to about 6 μm.

Figure 2B:
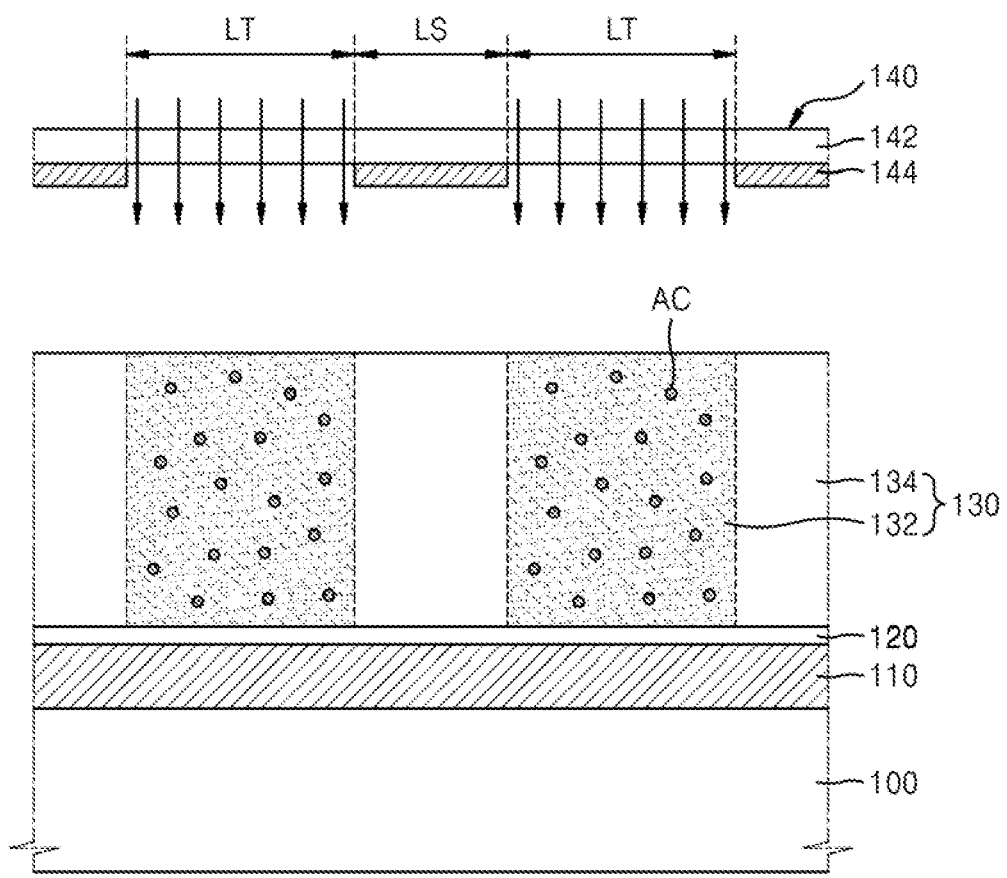

Referring to FIGS. 1 and 2B, in a process P20, a plurality of acids AC may be generated from the phenolic hydroxyl group (which is included in the compound represented by Chemical Formula 1) and the PAG, in a first region 132 of the photoresist layer 130 by exposing the first region 132 that is a portion of the photoresist layer 130, and the chemically amplified polymer and the compound represented by Chemical Formula 1 may be deprotected by the plurality of acids AC.

In an implementation, to expose the first region 132 of the photoresist layer 130, a photomask 140 having a plurality of light shielding areas LS and a plurality of light transmitting areas LT may be aligned at a certain position above the photoresist layer 130, and the first region 132 of the photoresist layer 130 may be exposed to light through the plurality of light transmitting areas LT of the photomask 140. To expose the first region 132 of the photoresist layer 130, a KrF excimer laser (248 nm), an ArF excimer laser (193 nm), an $F_2$ excimer laser (157 nm), or an EUV laser (13.5 nm) may be used.

The photomask 140 may include a transparent substrate 142, and a plurality of light shielding patterns 144 on the transparent substrate 142 in the plurality of light shielding areas LS. The transparent substrate 142 may include quartz. The plurality of light shielding patterns 144 may include chromium (Cr). The plurality of light transmitting areas LT may be defined by the plurality of light shielding patterns 144.

In an implementation, to diffuse the plurality of acids AC in the first region 132 of the photoresist layer 130, an annealing process may be performed. In an implementation, in the process 20 of FIG. 1, by annealing a result product, which is obtained after the first region 132 of the photoresist layer 130 is exposed to light, at a temperature of about 50° C. to about 150° C. at least some of the plurality of acids AC in the first region 132 may be diffused in the first region 132, thereby allowing the plurality of acids AC to be relatively uniformly distributed in the first region 132. The annealing may be performed for about 10 seconds to about 100 seconds. In an implementation, the annealing process may be performed at a temperature of about 100° C. for about 60 seconds.

In an implementation, to diffuse the plurality of acids AC in the first region 132 of the photoresist layer 130, a separate annealing process may not be performed. In this case, in the process P20 of FIG. 1, the plurality of acids AC may be diffused in the first region 132 of the photoresist layer 130 without the separate annealing process, during the exposure of the first region 132 of the photoresist layer 130.

As a result of the diffusion of the plurality of acids AC in the first region 132 of the photoresist layer 130, an acid-labile group in each of the chemically amplified polymer and the compound represented by Chemical Formula 1 may be deprotected in the first region 132, and the first region 132 of the photoresist layer 130 may be changed into a state of being able to be easily dissolved in an alkaline developer.

When a basic quencher is included in the photoresist layer 130, the basic quencher (which may be included in the photoresist layer 130 in a second region 134 that is an unexposed region) may function as a quenching base for neutralizing the undesired acids diffused into the second region 134 from the first region 132.

As described above, in the first region 132 that is an exposed region, the plurality of acids AC may be generated from the phenolic hydroxyl group (which is included in the compound represented by Chemical Formula 1) and the PAG, and as a result, the acid-labile group in each of the chemically amplified polymer and the compound represented by Chemical Formula 1 may be deprotected. Here, by deprotecting the acid-labile group included in the compound due to the acids generated by the exposure, the compound may be decomposed into a molecule having a carboxyl group (*—COOH) and thus have increased solubility in the developer. In addition, in the compound according to the embodiments, each of the organic groups respectively represented by $Ar^1$ and $Ar^2$ in Chemical Formula 1 may include at least one iodine atom, thereby improving the absorbance of the first region 132 of the photoresist layer 130 upon the exposure. In addition, in the compound according to the embodiments, each of the organic groups respectively represented by $Ar^1$ and $Ar^2$ in Chemical Formula 1 may include the phenolic hydroxyl group, thereby improving the sensitivity to an exposure light source. Accordingly, a difference in acidity between the first region 132, which is an exposed region, and the second region 134, which is an unexposed region, may be maximized, and thus, a difference in solubility between the exposed region and the unexposed region of the photoresist layer 130 with respect to the developer may be increased. Therefore, in a final pattern intended to be formed in the feature layer 110 in a subsequent process, a pattern having small line-edge roughness (LER) or small line-width roughness (LWR) may be obtained.

Figure 2C:
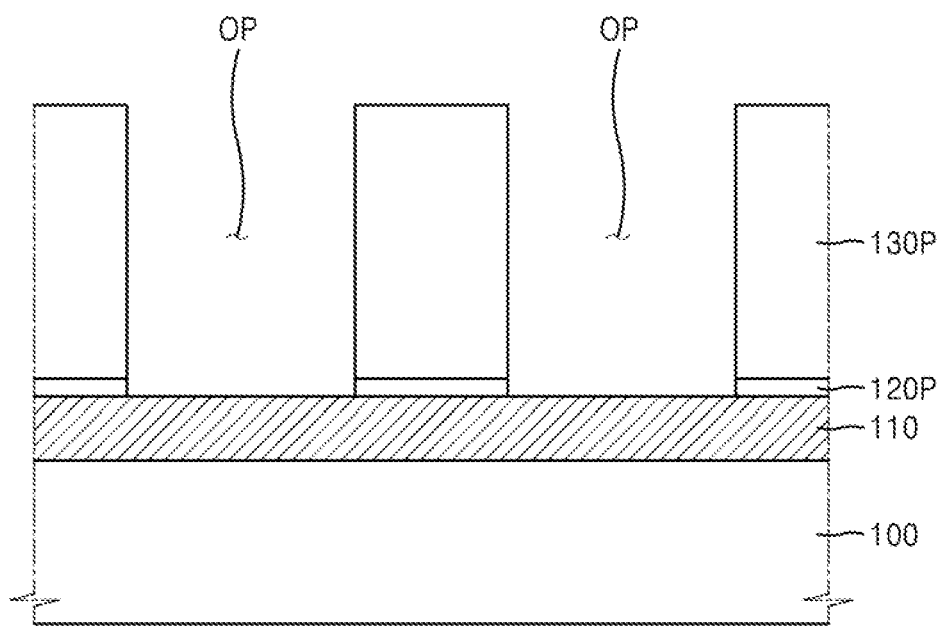

Referring to FIGS. 1 and 2C, in a process P30, the first region 132 of the photoresist layer 130 may be removed by developing the photoresist layer 130 by using a developer.

As a result, a photoresist pattern 130P including the unexposed second region 134 of the photoresist layer 130 may be formed.

The photoresist pattern 130P may include a plurality of openings OP. After the photoresist pattern 130P is formed, a DBARC pattern 120P may be formed by removing portions of the DBARC layer 120, which are exposed by the plurality of openings OP.

In an implementation, to develop the photoresist layer 130, an alkaline developer may be used. In an implementation, the alkaline developer may include, e.g., a 2.38 wt % tetramethylammonium hydroxide (TMAH) solution.

In a result product of FIG. 2B, because, in the first region 132 of the photoresist layer 130, the chemically amplified polymer and the compound according to Chemical Formula 1 are deprotected by the plurality of acids AC, the solubility of the first region 132 in the developer may be improved during the development of the photoresist layer 130 by the developer, thereby cleanly removing the first region 132. Therefore, after the photoresist layer 130 is developed, a vertical sidewall profile of the photoresist pattern 130P may be obtained without residual defects, such as a footing phenomenon or the like, occurring. As such, by improving the profile of the photoresist pattern 130P, when the feature layer 110 is processed by using the photoresist pattern 130P, a critical dimension of a region intended to be processed in the feature layer 110 may be precisely controlled.

Figure 2D:
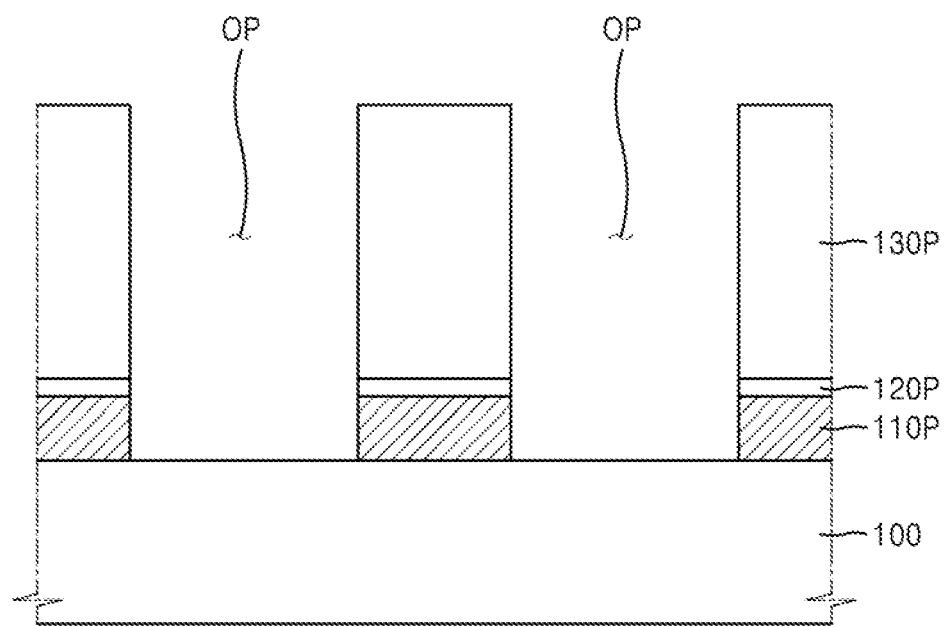

Referring to FIGS. 1 and 2D, in a process P40, in a result product of FIG. 2C, the underlayer may be processed by using the photoresist pattern 130P.

To process the underlayer, various processes, such as a process of etching the feature layer 110 exposed by the openings OP of the photoresist pattern 130P, a process of implanting impurity ions into the feature layer 110, a process of forming an additional layer on the feature layer 110 via the openings OP, a process of modifying a portion of the feature layer 110 via the openings OP, and the like, may be performed. FIG. 2I) illustrates a process of forming a feature pattern 110P by etching the feature layer 110 exposed by the openings OP, as an example process of processing the underlayer.

In an implementation, the process of forming the feature layer 110 may be omitted from the process described with reference to FIG. 2A, and in this case, instead of the process P40 of FIG. 1 and the process described with reference to FIG. 2D, the substrate 100 may be processed by using the photoresist pattern 130P. In an implementation, various processes, such as a process of etching a portion of the substrate 100 by using the photoresist pattern 130P, a process of implanting impurity ions into some regions of the substrate 100, a process of forming an additional layer on the substrate 100 via the openings OP, a process of modifying a portion of the substrate 100 via the openings OP, and the like, may be performed.

Figure 2E:
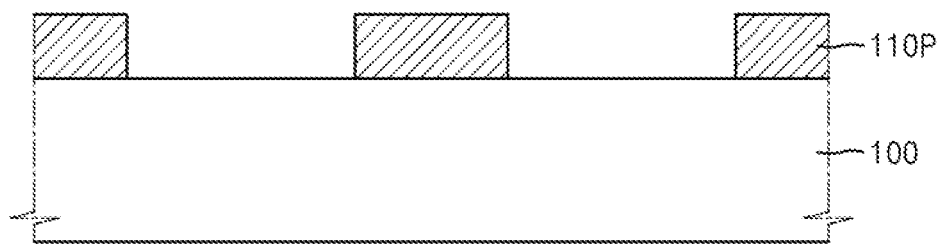

Referring to FIG. 2E, the photoresist pattern 130P and the DBARC pattern 120P, which remain on the feature pattern 110P, may be removed from a result product of FIG. 2D. To remove the photoresist pattern 130P and the DBARC pattern 120P, ashing and strip processes may be used.

In accordance with the method of manufacturing an integrated circuit device according to the embodiments as described with reference to FIGS. 1 and 2A to 2E, the difference in solubility in the developer between the exposed region and the unexposed region of the photoresist layer 130, which is obtained from the photoresist composition according to the embodiments, may be increased, and thus, the photoresist pattern 130P obtained from the photoresist layer 130 may have reduced LER and LWR and thus provide high pattern fidelity. Therefore, when a subsequent process is performed on the feature layer 110 and/or the substrate 100 by using the photoresist pattern 1301P, critical dimensions of processed regions or patterns, which are intended to be formed in the feature layer 110 or the substrate 100, may be precisely controlled, thereby improving the dimensional precision thereof. In addition, the critical dimension (CD) distribution of the patterns intended to be implemented on the substrate 100 may be uniformly controlled, and the productivity of a process of manufacturing an integrated circuit device may be improved.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Example 1

Synthesis of Compound Represented by Chemical Formula 2A

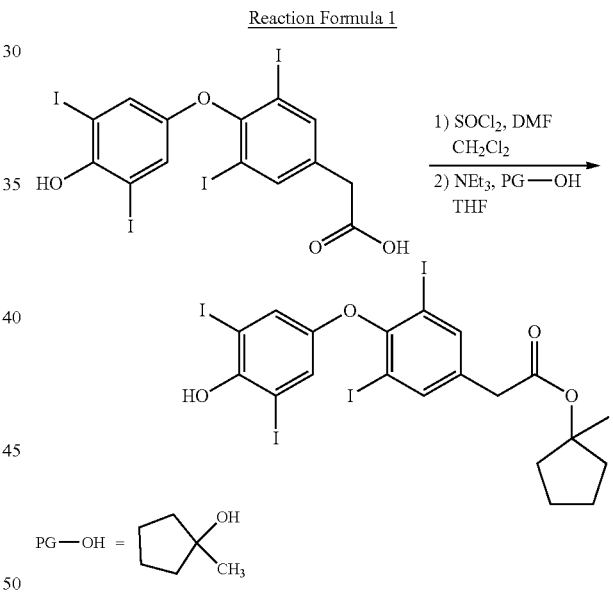

547 µL, (7.5 mmol) of thionyl chloride (SOCl$_2$) and 39 µL (0.5 mmol) of dimethylformamide (DMF) were added dropwise to a solution including 3.74 g (5.0 mmol) of tetraiodothyroacetic acid (tetrac) stirred together with 5.0 mL of anhydrous dichloromethane (CH$_2$Cl$_2$), in an ice-water bath maintained at 0° C. An obtained result product was stirred at ambient temperature for 2 hours, followed by evaporating an obtained reaction mixture at a reduced pressure, thereby obtaining an acyl chloride with a corresponding structure. The obtained acyl chloride was dissolved in 15.0 mL of anhydrous tetrahydrofuran (THF) without additional purification, and 2.09 ml. (15.0 mmol) of trimethylamine (NEt$_3$) and 831 µL (7.5 mmol) of 1-methylcyclopentanol as PG-OH were added dropwise to an obtained mixture in an ice-water bath maintained at 0° C. An obtained mixture was left at ambient temperature for 1 hour and then refluxed by heating for 8 hours. 100 mL of dichloromethane was added to an obtained reaction mixture, followed by performing cleaning by using 5 wt % hydrochloric acid (HCl) and 1 wt % aqueous ammonia in the stated order. Next, an organic phase was evaporated, followed by recrystallizing a crude product with ethanol, thereby obtaining 2.70 g (3.25 mmol) of the compound (1-methylcyclopentyl 2-(4-(4-hydroxy-3,5-diiodophenoxy)-3,5-diiodophenyl)acetate) represented by Chemical Formula 2A. (Yield 65.1%)

$^1$H-NMR (DMSO-d$_6$) δ(ppm): 7.89 (s, 2H), 7.15 (s, 2H), 5.71 (s, 1H), 3.65 (s, 2H), 1.51-1.78 (m, 8H), 1.36 (s, 3H)

Synthesis Example 2

Synthesis of Compound Represented by Chemical Formula 2C 2.49 g (2.90 mmol) of the compound (1-isopropylcyclopentyl 2-(4-(4-hydroxy-3,5-diiodophenoxy)-3,5-diiodophenyl)acetate) represented by Chemical Formula 2B was obtained in the same manner as in Synthesis Example 1 except that 0.96 g (7.5 mmol) of 1-isopropyleyclopentanol, instead of 1-methylcyclopentanol, was used as PG-OH. (Yield 58.0%)

$^1$H-NMR (DMSO-d$_6$) δ(ppm): 7.88 (s, 2H), 7.14 (s, 2H), 5.75 (s, 1H), 3.66 (s, 2H), 2.05 (m, 1H), 1.53-1.82 (m, 8H), 0.86 (d, 6H)

Synthesis Example 3

Synthesis of Compound Represented by Chemical Formula 21)

2.17 g (2.39 mmol) of the compound (1-phenylcyclohexyl 2-(4-(4-hydroxy-3,5-diiodophenoxy)-3,5-diiodophenyl)acetate) represented by Chemical Formula 2D was obtained in the same manner as in Synthesis Example 1 except that 1.32 g (7.5 mmol) of 1-phenylcyclohexanol, instead of 1-methylcyclopentanol, was used as PG-OH. (Yield 47.9%)

$^1$H-NMR (DMSO-d$_6$) δ (ppm): 7.85 (s, 2H), 7.10-7.59 (m, 7H), 6.01 (s, 1H), 3.71 (s, 2H), 2.05-2.15 (m, 2H), 1.80-1.90 (m, 2H), 1.30-1.65 (m, 6H)

By way of summation and review, techniques to help increase the photosensitivity in photolithography processes for manufacturing integrated circuit devices, and to help improve the dissolution contrast between exposed regions and unexposed regions of photoresist layers with respect to developer, may be considered.

One or more embodiments may provide a photosensitizing compound having an acid-labile protecting group.

One or more embodiments may provide a compound having a structure that has excellent sensitivity with respect to an exposure light source and excellent optical absorption properties.

One or more embodiments may provide a photoresist composition exhibiting improved photosensitivity and contrast in a photolithography process for manufacturing an integrated circuit device.

One or more embodiments may provide a method of manufacturing an integrated circuit device, the method being capable of improving the dimension precision of a pattern intended to be formed, by improving the photosensitivity in a photolithography process and improving the dissolution contrast between an exposed region and an unexposed region of a photoresist layer with respect to a developer.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound comprising Chemical Formula 1:

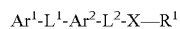     [Chemical Formula 1]

wherein, in Chemical Formula 1,

Ar$^1$ is an organic group including:
  a C6 to C30 aromatic ring, which includes at least one iodine atom and at least one hydroxyl group, or
  a C6 to C30 heterocyclic aromatic ring, which includes at least one iodine atom and at least one hydroxyl group, Ar$^2$ is an organic group including:
  a C6 to C30 aromatic ring, which includes at least one iodine atom, or
  a C6 to C30 heterocyclic aromatic ring, which includes at least one iodine atom, L$^1$ and L$^2$ are each independently a divalent linking group, the divalent linking group including —O—, —S—, —SO—, —SO$_2$—, —CO—, —O—CO—O—, —C(═O)O—, —OCO—, —CONH—, —NHCO—, —CO—, a substituted or unsubstituted C1 to C6 linear alkylene group, a substituted or unsubstituted C3 to C6 branched alkylene group, a substituted or unsubstituted C3 to C15 cycloalkylene group, a substituted or unsubstituted C2 to C6 alkenylene group, or a combination thereof, X is —C(═O)O— or —S(═O)$_2$—O—, and R$^1$ is an acid-labile protecting group including a substituted t-butyl group or a substituted or unsubstituted C3 to C30 tertiary alicyclic group.

2. The compound as claimed in claim 1, wherein:
the compound comprises Chemical Formula 2:

[Chemical Formula 2]

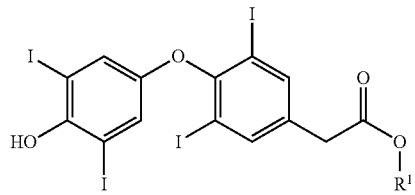

in Chemical Formula 2, R$^1$ is defined the same as R$^1$ that of Chemical Formula 1.

3. The compound as claimed in claim 1, wherein, in Chemical Formula 1, R$^1$ is a substituted or unsubstituted C3 to C30 tertiary alicyclic group.

4. The compound as claimed in claim 1, wherein:
a number of iodine atoms included in the compound of Chemical Formula 1 is at least 4, and
a total weight of the iodine atoms in the compound is at least 50 wt % based on a total weight of the compound.

5. The compound as claimed in claim 1, wherein:
$L^1$ is —O—, and
$L^2$ is —C(=O)O—.

6. The compound as claimed in claim 1, wherein the compound is a compound selected from the group consisting of Chemical Formula 2A, 2B, 2C, 2D, and 2E:

[Chemical Formula 2A]

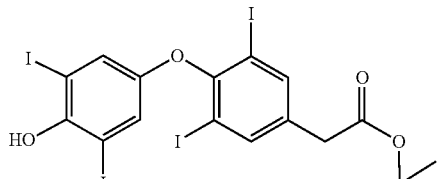

[Chemical Formula 2B]

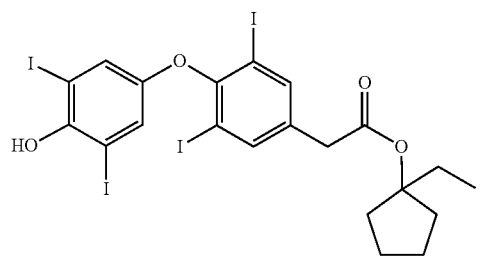

[Chemical Formula 2C]

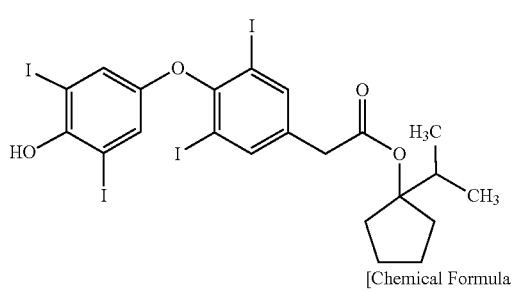

[Chemical Formula 2D]

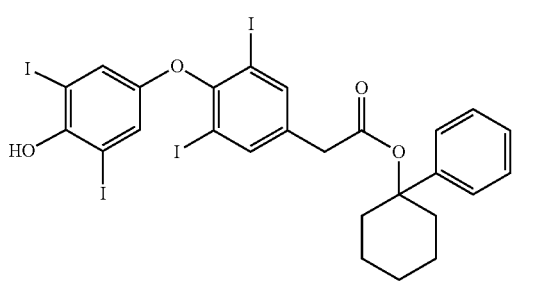

[Chemical Formula 2E]

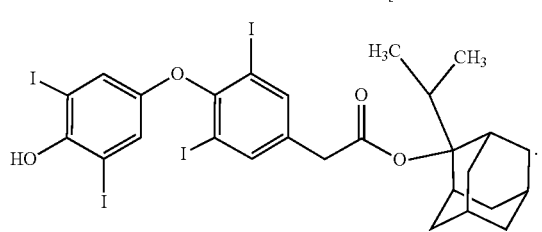

7. A photoresist composition comprising the compound as claimed in claim 1.

8. A photoresist composition, comprising:
a compound;
a chemically amplified polymer;
a photoacid generator (PAG); and
a solvent,
wherein the compound comprises Chemical Formula 1:

$Ar^1$-$L^1$-$Ar^2$-$L^2$-X—$R^1$ [Chemical Formula 1]

wherein, in Chemical Formula 1,
$Ar^1$ is an organic group including:
  a C6 to C30 aromatic ring, which includes at least one iodine atom and at least one hydroxyl group, or
  a C6 to C30 heterocyclic aromatic ring, which includes at least one iodine atom and at least one hydroxyl group,
$Ar^2$ is an organic group including:
  a C6 to C30 aromatic ring, which includes at least one iodine atom, or
  a C6 to C30 heterocyclic aromatic ring, which includes at least one iodine atom,
$L^1$ and $L^2$ are each independently a divalent linking group, the divalent linking group including —O—, —S—, —SO—, —SO$_2$—, —CO—, —O—CO—O—, —C(=O)O—, —OCO—, —CONH—, —NHCO—, —CO—, a substituted or unsubstituted $C_1$ to $C_6$ linear alkylene group, a substituted or unsubstituted $C_3$ to $C_6$ branched alkylene group, a substituted or unsubstituted $C_3$ to C15 cycloalkylene group, a substituted or unsubstituted $C_2$ to $C_6$ alkenylene group, or a combination thereof,
X is —C(=O)O— or —S(=O)$_2$—O—, and
$R^1$ is an acid-labile protecting group including a substituted or unsubstituted t-butyl group or a substituted or unsubstituted C3 to C30 tertiary alicyclic group.

9. The photoresist composition as claimed in claim 8, wherein:
the compound comprises Chemical Formula 2:

[Chemical Formula 2]

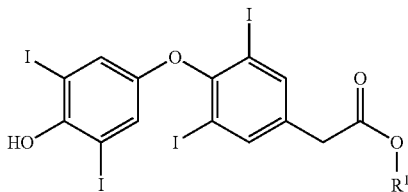

in Chemical Formula 2, $R^1$ is defined the same as $R^1$ that of Chemical Formula 1.

10. The photoresist composition as claimed in claim 8, wherein, in Chemical Formula 1, $R^1$ is a substituted or unsubstituted C3 to C30 tertiary alicyclic group.

11. The photoresist composition as claimed in claim 8, wherein the compound includes at least four iodine atoms.

12. The photoresist composition as claimed in claim 8, wherein, in Chemical Formula 1:
$L^1$ is —O—, and
$L^2$ is —C(=O)O—.

13. The photoresist composition as claimed in claim 8, wherein the compound is a compound selected from the group consisting of Chemical Formula 2A and 2B:

[Chemical Formula 2A]

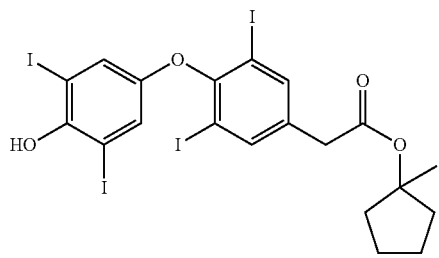

[Chemical Formula 2B]

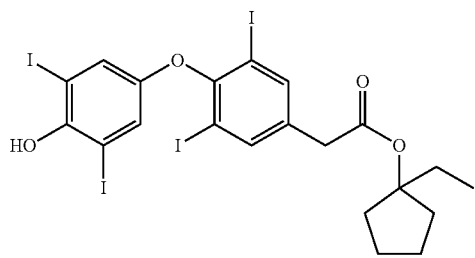

14. The photoresist composition as claimed in claim 8, wherein the compound comprises Chemical Formula 2C:

[Chemical Formula 2C]

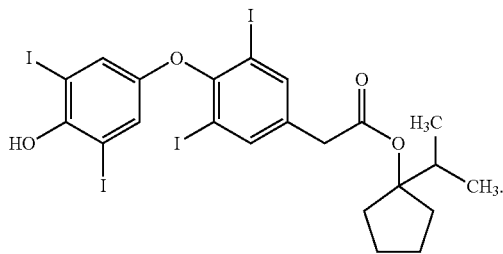

15. The photoresist composition as claimed in claim 8, wherein the compound comprises Chemical Formula 2D:

[Chemical Formula 2D]

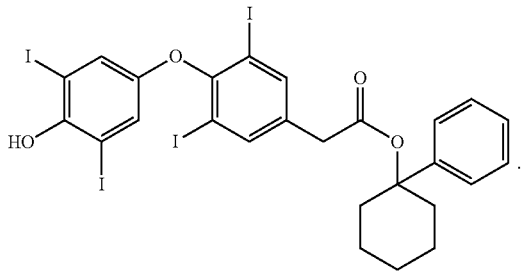

16. The photoresist composition as claimed in claim 8, wherein the compound comprises Chemical Formula 2E:

[Chemical Formula 2E]

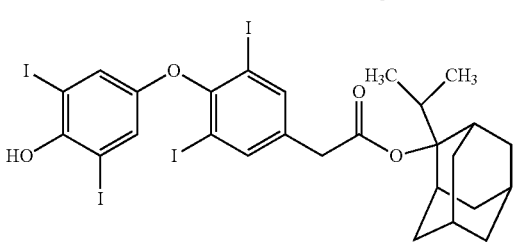

17. A method of manufacturing an integrated circuit device, the method comprising:
forming a photoresist layer on an underlayer by using a photoresist composition including a compound, a chemically amplified polymer, a photoacid generator (PAG), and a solvent, the compound including a phenolic hydroxyl group, a plurality of iodine atoms, and an acid-labile protecting group;
generating a plurality of acids from the phenolic hydroxyl group and the PAG in a first region of the photoresist layer by exposing the first region, and deprotecting the chemically amplified polymer and the compound by the plurality of acids;
forming a photoresist pattern including an unexposed region of the photoresist layer by removing the exposed first region of the photoresist layer by using a developer; and
processing the underlayer by using the photoresist pattern.

18. The method as claimed in claim 17, wherein:
the compound comprises Chemical Formula 1:

$Ar^1-L^1-Ar^2-L^2-X-R^1$     [Chemical Formula 1]

in Chemical Formula 1,
$Ar^1$ is an organic group including:
a C6 to C30 aromatic ring, which includes at least one iodine atom and at least one hydroxyl group, or
a C6 to C30 heterocyclic aromatic ring, which includes at least one iodine atom and at least one hydroxyl group,
$Ar^2$ is an organic group including:
a C6 to C30 aromatic ring, which includes at least one iodine atom, or
a C6 to C30 heterocyclic aromatic ring, which includes at least one iodine atom,
$L^1$ and $L^2$ are each independently a divalent linking group, the divalent linking group including —O—, —S—, —SO—, —SO$_2$—, —CO—, —O—CO—O—, —C(=O)O—, —OCO—, —CONH—, —NHCO—, —CO—, a substituted or unsubstituted C1 to C6 linear alkylene group, a substituted or unsubstituted C3 to C6 branched alkylene group, a substituted or unsubstituted C3 to C15 cycloalkylene group, a substituted or unsubstituted C2 to C6 alkenylene group, or a combination thereof,
X is —C(=O)O— or —S(=O)$_2$—O—, and
$R^1$ is an acid-labile protecting group including a substituted or unsubstituted t-butyl group or a substituted or unsubstituted C3 to C30 tertiary alicyclic group.

19. The method as claimed in claim 17, wherein:
the compound comprises Chemical Formula 2:

[Chemical Formula 2]

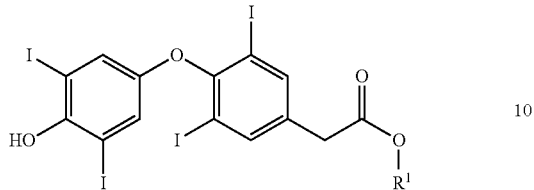

in Chemical Formula 2, $R^1$ is an acid-labile protecting group including a substituted or unsubstituted t-butyl group or a substituted or unsubstituted C3 to C30 tertiary alicyclic group).

20. The method as claimed in claim 17, wherein the photoresist composition further includes a basic quencher.

* * * * *